United States Patent [19]
Utsumi et al.

[11] Patent Number: 5,888,194
[45] Date of Patent: Mar. 30, 1999

[54] ENDOSCOPE INCLUDING AN IMPROVED LIGHTING APPARATUS

[75] Inventors: Atsushi Utsumi; Koji Okawa; Masahiro Miura, all of Itami, Japan

[73] Assignee: Mitsubishi Cable Industries, Inc., Amagasaki, Japan

[21] Appl. No.: 764,781

[22] Filed: Dec. 12, 1996

[30] Foreign Application Priority Data

Dec. 14, 1995 [JP] Japan .................................. 7-347794
Dec. 14, 1995 [JP] Japan .................................. 7-347795

[51] Int. Cl.[6] ........................................................ A61B 1/07
[52] U.S. Cl. ........................... 600/182; 600/178; 385/117
[58] Field of Search ................................... 600/178, 182, 600/199, 200; 385/34, 43, 117, 902

[56] References Cited

U.S. PATENT DOCUMENTS

| | | | |
|---|---|---|---|
| 2,235,979 | 3/1941 | Brown | 600/178 |
| 3,779,628 | 12/1973 | Kapron et al. | 385/43 |
| 4,729,621 | 3/1988 | Edelman | 600/182 |
| 4,807,954 | 2/1989 | Oyamada et al. | 385/43 |
| 4,870,952 | 10/1989 | Martinez | 600/182 |
| 5,479,545 | 12/1995 | Davenport et al. | 385/43 |
| 5,513,291 | 4/1996 | Buchin et al. | 385/93 |
| 5,630,783 | 5/1997 | Steinberg | 600/160 |
| 5,718,664 | 2/1998 | Peck et al. | 600/178 |
| 5,746,494 | 5/1998 | Koeda et al. | 385/117 |

*Primary Examiner*—John P. Leubecker
*Attorney, Agent, or Firm*—Armstrong, Westerman, Hattori, McLeland & Naughton

[57] ABSTRACT

An endoscope provided with a lighting apparatus. In this lighting apparatus, a tapered fiber is applied between a lamp and a base end face of a light guide. This taper fiber is in a tapered configuration which gradually diminishes in diameter toward an end side. The lamp is a high luminance lamp of a low outgoing angle. The lamp, a battery, and the tapered fiber of the lighting apparatus are arranged unitedly on a grip portion of the endoscope.

6 Claims, 7 Drawing Sheets

ENDOSCOPE INCLUDING AN IMPROVED LIGHTING APPARATUS

BACKGROUND OF THE INVENTION

1. Field of the Invention This invention relates to an endoscope.

2. Description of the Related Art

Various kinds of endoscopes have been conventionally used for medical examination and medical treatment. However, in these conventional endoscopes, an endoscope main body and a lighting apparatus for providing light into its light guide are formed separately. The endoscope main body and the lighting apparatus are connected through a cord having a light guide, and the endoscope main body has been operated (used) with said lighting apparatus placed separately.

A conventional lighting apparatus is provided with a lamp of several tens or several hundreds watts (W), and is heavy and large, which causes inconvenience in carrying the lighting apparatus.

In some conventional lighting apparatuses, a battery is used for convenience in carrying, but coupling efficiency between the lamp and the light guide inside the endoscope, i.e. proportion (percentage) of quantity of light which is effectively incident on the light guide among a total luminescence luminous flux of the lamp, is only one percent at most, and this illuminance is insufficient for actual use. It is necessary to use a light source of a big power in order to obtain sufficient illuminance, and consequently, it is necessary to store the power supply system separately in a pocket and use a cooling fan.

In conventional endoscopes, a lighting apparatus is large and heavy, and is separated from a main body of the endoscope. This causes inconvenience in conveying the endoscope, and a large amount of power consumption is required. When a battery is used for the lighting apparatus as described above, the endoscope is also inconvenient because the illuminance is insufficient or it is necessary to store the power supply system separately in a pocket.

It is therefore an object of the present invention to provide an endoscope wherein the endoscope is easily handled and operated, it is possible to carry the endoscope, and it is possible to insert the endoscope into a human body more easily, swiftly, accurately, and safely in medical examination or medical treatment.

It is another object of the present invention to provide an endoscope wherein the power consumption is diminished, usage for long hours is possible, and sufficient illuminance is obtained.

BRIEF DESCRIPTION OF THE DRAWINGS

The present invention will be described with reference to the accompanying drawings, in which.

DESCRIPTION OF THE PREFERRED EMBODIMENTS

Preferred embodiments of the present invention will now be described with reference to the accompanying drawings.

Figure 4:
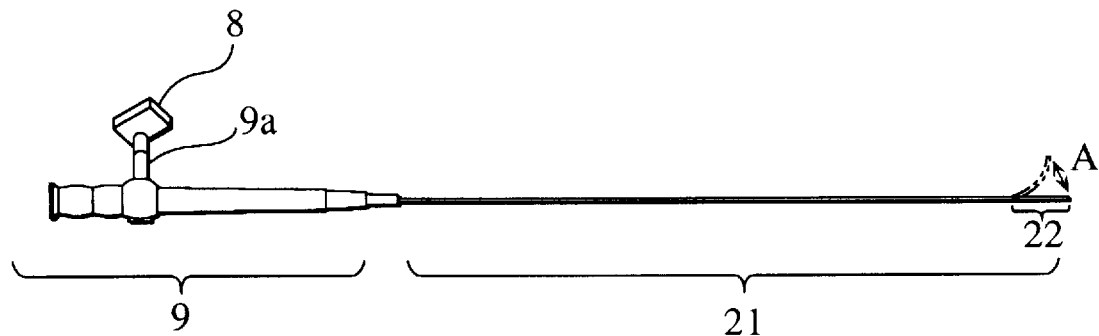
FIG. 4 is a whole view of an endoscope according to the present invention.
Figure 5:
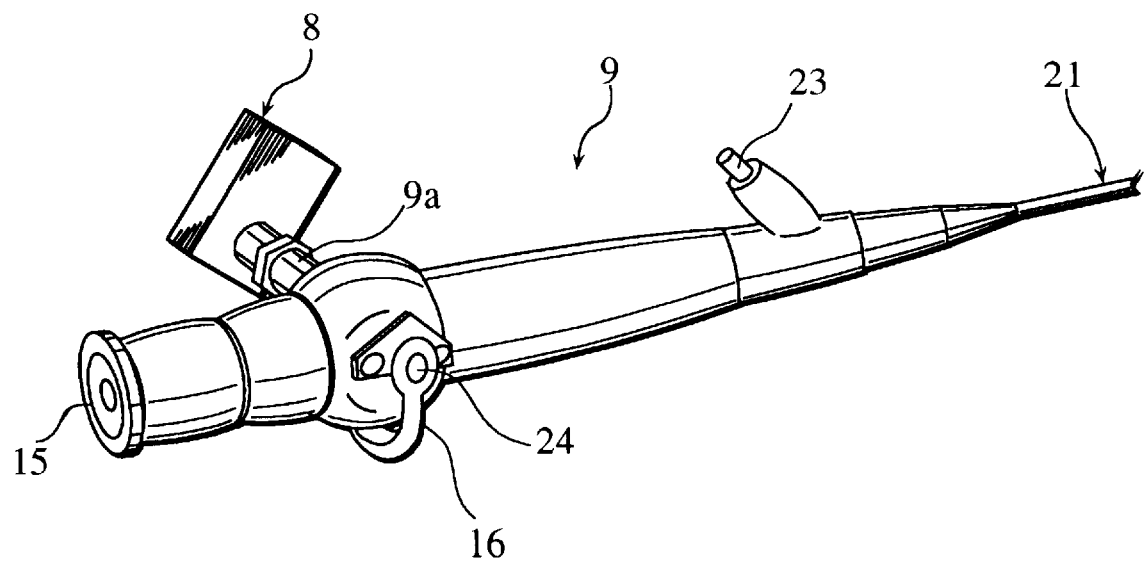
FIG. 5 is a perspective view of a principal portion.
Figure 6:
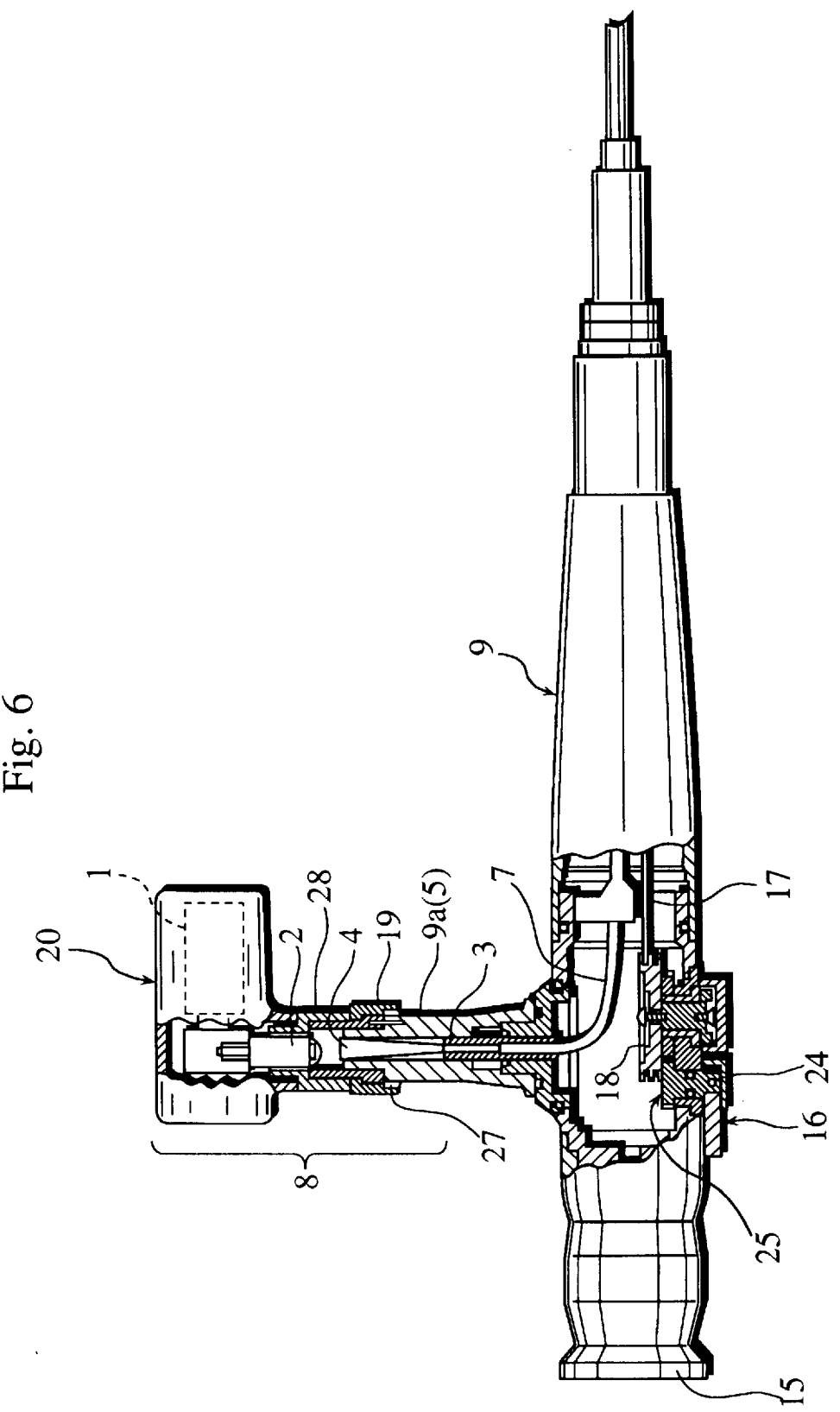
FIG. 6 is an enlarged view of a principal portion shown with a portion cutaway.

An endoscope shown in FIG. 4 to FIG. 6 possesses a grip portion 9 which can be held with one hand and an insertion portion 21 extending forward from the grip portion 9. The grip portion 9 possesses an eyepiece portion 15 at its base end and a freely oscillating distal bending controlling portion 16 at its middle portion.

A lighting apparatus 8 is unitedly arranged on the grip portion 9. That is to say, the lighting apparatus 8 is directly (without a cord having a light guide) attached to a rigid protruding branch portion 9a.

The insertion portion 21 has appropriate flexibility and rigidity against pressure, and is provided with a distal portion 22 to be bent at its end which freely advances and curves as shown with an arrow A in FIG. 4. In the inserting portion 21, an image guide, a light guide 3 (see FIG. 6), a wire 17 for bending distal portion (see FIG. 6), and a tube for working channel are inserted inside an outermost protecting tube (which outer diameter is arranged to be, for example, at least 5 mm). In FIG. 5, 23 indicates a working channel connection portion.

The controlling portion 16 in a L-shaped or U-shaped configuration is fixed at a rotational axis 24. It is possible to rotate a wire reel 18 through a reduction gear 25 by oscillating the controlling portion 16, thereby the distal portion 22 to be bent at the end of the insertion portion 21 can be oscillated.

Figure 7:
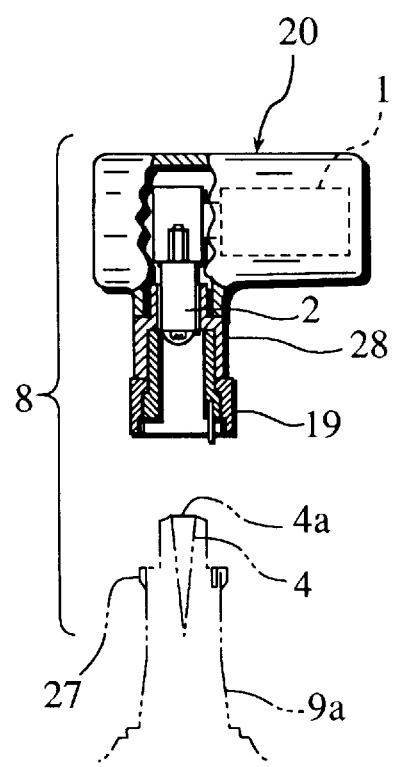
FIG. 7 is an explanatory view showing detachability.

As shown in FIG. 6 and FIG. 7, it is arranged so that a part (or the whole) of the lighting apparatus 8 is detachable from the grip portion 9. The lighting apparatus 8 is provided with a lamp 2, a battery 1 (as a power source), and a tapered fiber 4 having a tapered configuration which diameter diminishes toward the end side. In this case, the lighting apparatus 8 protrudes from the grip portion 9 toward a direction that intersects perpendicularly with an axis of the grip portion 9. It is possible to arrange the lighting apparatus 8 to intersect the axis of the grip portion 9 at an angle besides 90°.

In the illustration in FIG. 6 and FIG. 7, the tapered fiber 4 is fixed inside the branch portion 9a which protrudes from the grip portion 9, and an incident end 4a having a big diameter appears outside under a detached situation shown in FIG. 7. A male screw portion 27 is formed on an outer circumference of the end of the branch portion 9a, parts in the lighting apparatus 8 excluding the tapered fiber are stored in a casing 20, a cap nut 19 is arranged on an end of a protruding cylindrical portion 28, and the cap nut 19 fits unitedly and detachably with the male screw portion 27.

In order to arrange the lighting apparatus 8 unitedly on the grip portion 9 as shown in FIG. 4 to FIG. 7 for actual use as an endoscope, it is indispensable to diminish this lighting apparatus in size and weight and arrange an effective quantity of light to be incident from a base end face of the light guide 3, therefore the lighting apparatus 8 is composed as described below in the present invention.

Figure 1:
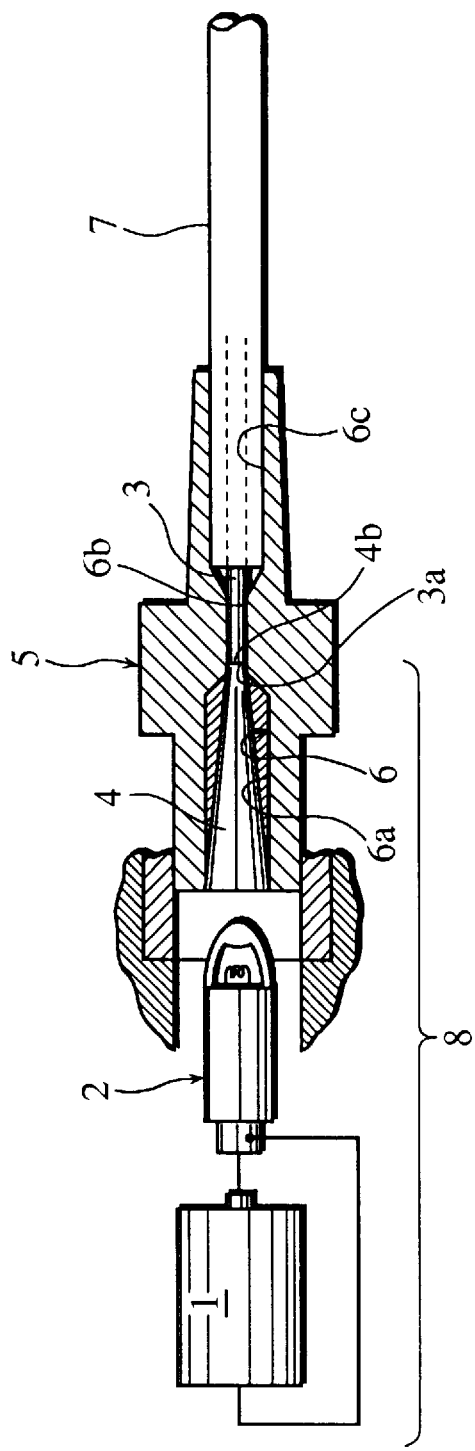
FIG. 1 is an enlarged explanatory view of a principal portion of the present invention.
Figure 2:
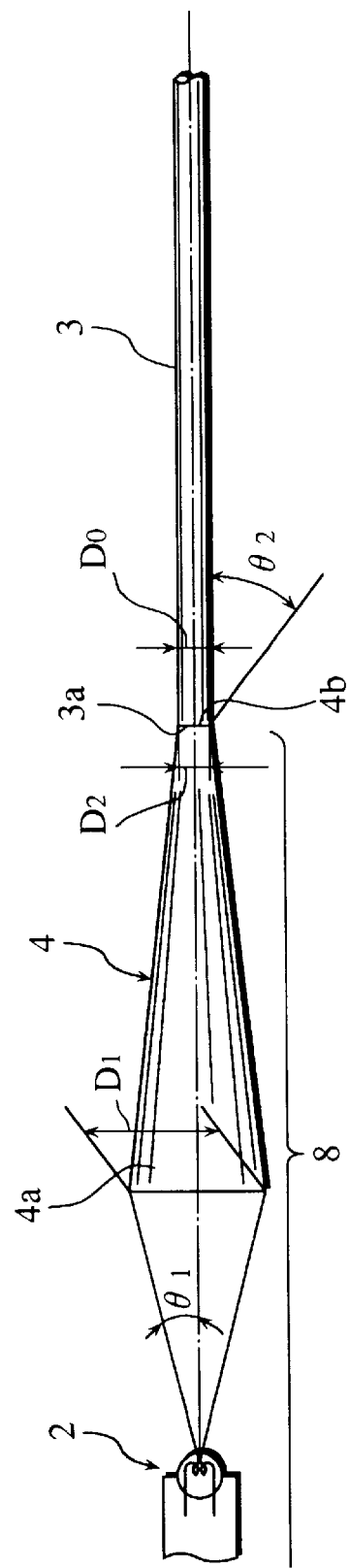
FIG. 2 is an explanatory view of an epitome of the present invention.

That is to say, in FIG. 1 and FIG. 2, the lamp 2 as the light source is a (highly convergent) high luminance lamp of a low outgoing angle. A lamp as shown in FIG. 2, wherein a proportion of the light elements which outgoing angles $2\theta_1$ are at most 20° is at least half of the forward total quantity of light, is herein described as "a high luminance lamp of a low outgoing angle". The lamp 2 can be a lamp of any kind and any structure provided these conditions are satisfied, for example, a halogen lamp having a lens structure unitedly on an end portion of a lamp glass bulb.

It is preferable to use a lithium battery as the battery 1 and utilize its advantage of being small sized and long-life. It is also possible to use a nickel-cadmium battery, a primary electrical cell, or a secondary battery. The tapered fiber 4 is applied between the lamp 2 and the base end face 3a of the light guide 3. The tapered fiber 4 is used to guide the outgoing light to the end with low-loss and increasing light density toward the light guide 3, and gradually diminishes in diameter toward the end side. It is possible to use a halogen lamp as the lamp 2, and a halogen lamp with an end lens of approximately 1 W to 10 W is suitable.

This tapered fiber 4 is produced by (heating and) lengthening a multicomponent glass fiber preform, and is arranged to be at least 0.4 in characteristic numerical aperture $NA_0$.

In other words, it is arranged so that $NA_0 \geq 0.4$.

In FIG. 1, 5 indicates a part of a light guide plug. The tapered fiber 4 is inserted into a base end side hole portion 6a of an axis hole 6 of the light guide plug 5 and fixed with adhesive, and an outgoing end 4b at an end of the tapered fiber 4 is inserted into a middle small diameter hole portion 6b of the axis hole 6. 7 is a cover of the light guide 3, and a base end portion of the cover 7 is inserted into an end side hole portion 6c of the light guide plug 5, a base end face of the light guide 3 which slightly appears and protrudes from the base end face of the cover 7 is inserted into the middle small diameter hole portion 6b and placed to face with the outgoing end 4b of the tapered fiber 4 closely or with a minute space.

Figure 3:
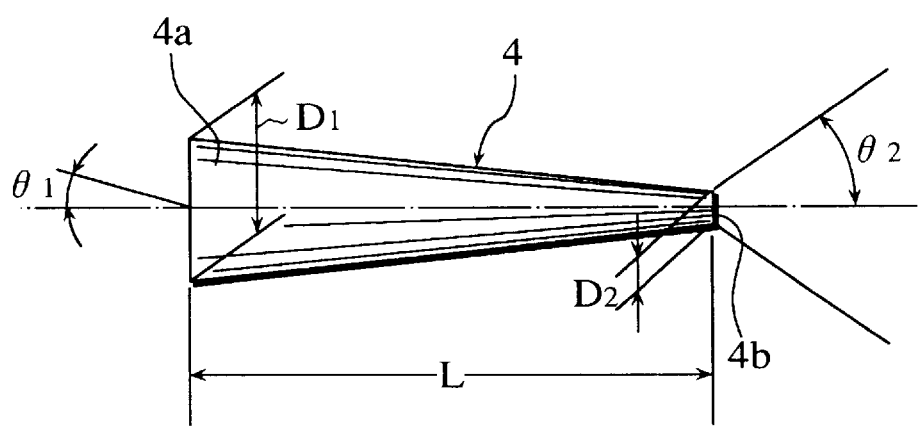
FIG. 3 is an explanatory view of a tapered fiber.

FIG. 2 and FIG. 3 are enlarged and simplified explanatory views illustrating a principal portion of FIG. 1 or FIG. 6, and as shown in FIG. 2 and FIG. 3, indicating an outer diameter of the incident end 4a (having a big diameter) of the tapered fiber 4 as $D_1$, a numerical aperture of the incidence as $NA_1$, an outer diameter of the outgoing end 4b as $D_2$, a numerical aperture of the outgoing as $NA_2$, an outer diameter of the light guide 3 as $D_0$, and (as described above,) a characteristic numerical aperture of the tapered fiber 4 (which is determined by a refractive index between the core and the clad) as $NA_0$, dimensions and characteristics of each portion are arranged satisfying the following numerical formula (1), numerical formula (2), and numerical formula (3).

$$0.9 \leq D_2/D_0 \leq 1.5 \quad (1)$$

$$1.1 \geq (D_1 \cdot NA_1)/(D_2 \cdot NA_2) \geq 0.7 \quad (2)$$

$$NA_2 \leq 1.1 \cdot NA_0 \quad (3)$$

In the foregoing numerical formula (1), when the value is less than 0.9, the diameter of the outgoing end 4b of the tapered fiber 4 becomes extremely small in comparison with the diameter of the light guide base end face 3a, and a large portion in a section of the light guide 3 is not utilized effectively. On the contrary, when the value is over 1.5, a large portion of the light quantity ejected from the outgoing end 4b of the tapered fiber 4 becomes wasteful (is not effectively transmitted into the light guide 3).

In the numerical formula (2), when the value is less than 0.7, the ability of the tapered fiber 4 to increase light density is not utilized effectively, which causes ineffectiveness. On the contrary, when the value is over 1.1, the amount of energy of light which leaks from the tapered fiber 4 becomes large, which causes generation of heat.

When the value does not satisfy the numerical formula (3), generation of heat occurs as well as when the value does not satisfy the numerical formula (2).

The battery 1 is used as the power source, the lithium battery is light, small, and has a long life, and the output voltage and current are stable, and these are advantages of the present invention. It is preferable to use a lithium battery of at most 10 V. The lamp 2 is a high luminance lamp of a low outgoing angle, and a halogen lamp with an end lens of approximately 1 W to 10 W (more preferably not exceeding 5 W) is suitable. A cordless endoscope composed as shown in FIG. 4 to FIG. 7 is arranged so that the endoscope can be easily carried, enlarges range of the operator to act and use the endoscope, and is convenient for diagnosis and medical treatment. Provided a part or the whole of the lighting apparatus 8 is arranged to be detachable, it is possible to disassemble the endoscope and store it easily in a bag or a case when carrying the endoscope. In this case, the casing 20 where the battery 1 and the lamp 2 are stored is also detachable, therefore it is possible to detach the casing 20 and connect the endoscope to a stationary type lamp through an extension light guide cord and conduct stabilized observation.

Figure 8A:
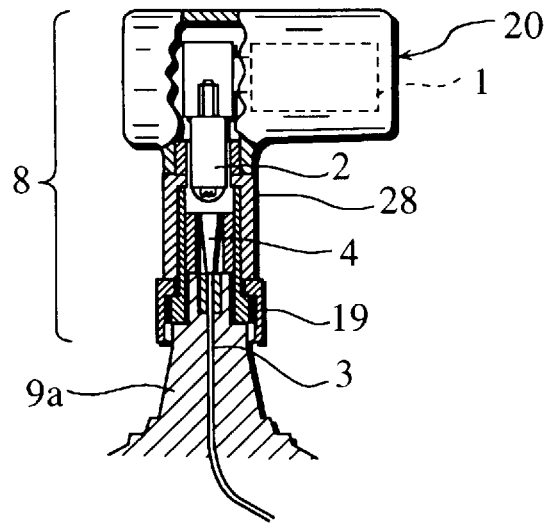
FIG. 8A shows a sectional view of another endoscope of the present invention with a lighting apparatus attached to the endoscope.
Figure 8B:
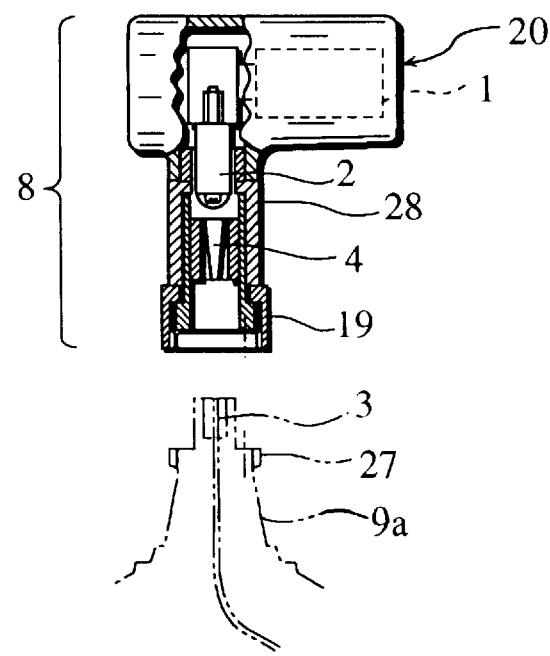
FIG. 8B is a sectional view wherein the lighting apparatus is separated from the endoscope.

FIG. 8A and FIG. 8B show another embodiment of the present invention, and it is possible to change the endoscope from attached (connected) situation as shown in FIG. 8A to a detached (separated) situation as shown in FIG. 8B. In this case, a tapered fiber 4 is arranged at a casing (a lamp case) 20 side and is detached from a branch portion 9a of a grip portion 9 unitedly with a lamp 2 and a battery 1. A base end of the light guide 3 is arranged at an end of the branch portion 9a, and detachment is made through, for example, a cap nut 19. Described below is an experimental example.

A halogen lamp of 2.5 V and 1.7 W with characteristics shown in Table 1 was used as the lamp 2.

TABLE 1

| Items | Measurement | | | | |
|---|---|---|---|---|---|
| L (distance from the lamp; mm) | 0 | 10 | 20 | 40 | 100 |
| Forward Illuminance (×10⁴; 1x) | 15 | 7.3 | 5.3 | 2.4 | 0.4 |
| Divergent Angle | | 7 | 14 | 17 | 28 |
| NA | | 0.06 | 0.12 | 0.17 | 0.24 |

In this experiment, the tapered fiber 4 is, with the core and the clad made of multicomponent glass, 0.62 in characteristic numerical aperture $NA_0$, 3.6 mm in incident end diameter $D_1$, 1.28 mm in outgoing end diameter, and 38 mm in length L. Nineteen plastic fibers each of which is 0.5 in numerical aperture NA and 250 microns in outer diameter were used as the light guide 3. A lithium battery of 3 V was used as the battery 1.

Table 2 shows results of measuring illuminance under the foregoing conditions.

TABLE 2

| Lighting Time | Illuminance (1x) Distance from the Light Guide (mm) | | |
|---|---|---|---|
| (min.) | 0 mm | 20 mm | 40 mm |
| 0 | 41,000 | 5,500 | 1,250 |
| 10 | 41,000 | 5,400 | 1,400 |
| 20 | 40,000 | 5,400 | 1,350 |
| 30 | 40,000 | 5,300 | 1,300 |

From Table 1 and Table 2, coupling efficiency B of the lighting apparatus 8 and the light guide 3 becomes extremely high as shown in the following numerical formula (4).

$$B = \frac{4.1 \times 10^4}{15 \times 10^4} \times 100 = 27.3\% \quad (4)$$

The following is a measurement result of using a conventional example for comparison wherein a metal-halide lamp of 200 W was used as the light source. In this case, the total amount of luminescence luminous flux was 250 lm, and when a light guide composed by seven plastic fibers of 250 microns (directly) received the luminescence luminous flux, in case the outer diameter of the light guide is 0.75 mm and the lighting area is 0.2 mm² (distance: 5 mm), the quantity of light becomes 4 lm ($lx/m^2$), and the coupling efficiency B is extremely low as shown in the following numerical formula (5).

$$B = \frac{4}{6250} \times 100 = 0.64\% \quad (5)$$

It is also preferable to use the endoscope of the present invention as a fiber scope for use in industrial application which is small, light, and handy to carry.

According to the present invention, the endoscope is easily handled and operated, and it is possible to carry the endoscope. Moreover, it is possible to insert the endoscope into a human body more easily, swiftly, accurately, and safely in medical examination or medical treatment. The endoscope is arranged to be small and light, and is handy to carry. Especially it is needless to store the battery 1 and the lamp 2 in the grip portion 9, therefore the grip portion 9 can be diminished in diameter, and this increases usability. It is possible to send approximately 5 to 10 percent of the forward total amount of luminous flux toward the light guide 3, the coupling efficiency is extremely improved, the power consumption is diminished, usage for long hours is possible, and sufficient illuminance is obtained. The light guide plug 5 connects the light guide 3 and the tapered fiber 4 with stability, and light of the light source lamp is effectively transmitted to the light guide. It is possible to connect this endoscope to a stationary type lamp through an extension light guide cord, therefore it is possible to obtain sufficient illuminance for hours and conduct stable observation using this endoscope.

While preferred embodiments of the present invention have been described in this specification, it is to be understood that the invention is illustrative and not restrictive, because various changes are possible within the spirit and indispensable features.

What is claimed is:

1. An endoscope wherein a lighting apparatus having a tapered fiber for transmitting light to a grip portion, a lamp for irradiating light on a base end face of said tapered fiber, and a battery as a power source of said lamp is arranged unitedly on the grip portion of the endoscope, wherein the lighting apparatus is provided with a light guide plug, which possesses a base end side hole portion where the tapered fiber in inserted, an end side hole portion where a base end portion of a light guide cover is inserted, and a middle small diameter hole portion for connecting said end side hole portion and the base end side hole portion where an end portion of the light guide protruding from a base end of the light guide cover and an end portion of the tapered fiber are inserted with said base end face of the light guide and an end face of the tapered fiber arranged to face each other closely or with a minute space.

2. The endoscope as set forth in claim 1, wherein the lamp is a high luminance lamp of a low outgoing angle, the battery is a lithium battery, and the tapered fiber is arranged to diminish in diameter gradually toward an end side where light is transmitted to the base end face of the light guide.

3. The endoscope as set forth in claim 1, wherein at least the battery and the lamp among the lighting apparatus are stored in a casing, said casing is freely attached to and separated from the grip portion, and said grip portion is adaptable to be mated with an extension light guide cord guiding light emitted by a stationary type lamp.

4. An endoscope wherein a lighting apparatus having a high luminance lamp of a low outgoing angle, a lithium battery, and a tapered fiber which diminishes in diameter gradually toward an end side is attached to a grip portion unitedly, said tapered fiber is arranged between said lamp and a base end face of a light guide, and when an outer diameter of an incident end of said tapered fiber is expressed as $D_1$, a numerical aperture of incidence of the tapered fiber as $NA_1$, an outer diameter of an outgoing end of the tapered fiber as $D_2$, a numerical aperture of outgoing of the tapered fiber as $NA_2$, an outer diameter of the light guide as $D_0$, and a characteristic numerical aperture of the tapered fiber obtained from a refractive index between its core and clad as $NA_0$, $$0.9 \leq D_2/D_0 \leq 1.5,$$
$$1.1 \geq (D_1 \cdot NA_1)/(D_2 \cdot NA_2) \geq 0.7, \text{ and}$$
$$NA_2 \leq 1.1 \cdot NA_0$$

are satisfied.

5. The endoscope as set forth in claim 4, wherein the tapered fiber is made of multicomponent glass fiber preform and a characteristic numerical aperture NA of the tapered fiber is at least 0.4.

6. The endoscope as set forth in claim 4, wherein the lighting apparatus is provided with a light guide plug, which possesses a base end side hole portion where the tapered fiber is inserted, an end side hole portion where a base end portion of a light guide cover is inserted, and a middle small diameter hole portion for connecting said end side hole portion and the base end side hole portion where an end portion of the light guide protruding from a base end of the light guide cover and an end portion of the tapered fiber are inserted with said base end face of the light guide and an end face of the tapered fiber arranged to face each other closely or with a minute space.

* * * * *